United States Patent
Muhamad et al.

(10) Patent No.: US 12,403,166 B2
(45) Date of Patent: Sep. 2, 2025

(54) *LABISIA PUMILA* EXTRACT COMPOSITION AND ITS PHARMACEUTICAL FORMULATION (71) Applicant: MEDIKA NATURA SDN. BHD., Selangor (MY)

(72) Inventors: Mustadza Muhamad, Selangor (MY); Abdul Razak Mohd Isa, Selangor (MY)

(73) Assignee: MEDIKA NATURA SDN. BHD., Selangor (MY)

( * ) Notice: Subject to any disclaimer, the term of this patent is extended or adjusted under 35 U.S.C. 154(b) by 385 days.

(21) Appl. No.: 17/961,940

(22) Filed: Oct. 7, 2022

(65) Prior Publication Data
US 2023/0134529 A1 May 4, 2023

(30) Foreign Application Priority Data

Nov. 2, 2021 (MY) .............................. PI2021006446

(51) Int. Cl.
*A61K 36/185* (2006.01)
(52) U.S. Cl.
CPC .................................. *A61K 36/185* (2013.01)
(58) Field of Classification Search
None
See application file for complete search history.

(56) References Cited

U.S. PATENT DOCUMENTS

| 7,879,368 B2 | 2/2011 | Yusoff et al. |
| 9,358,260 B2 | 6/2016 | Zulkarnaini et al. |

FOREIGN PATENT DOCUMENTS

| WO | WO2009116848 A1 | 9/2009 |
| WO | WO2013112040 A1 | 8/2013 |
| WO | WO2016093692 A1 | 6/2016 |

*Primary Examiner* — Michael V Meller
(74) *Attorney, Agent, or Firm* — MUNCY, GEISSLER, OLDS & LOWE, P.C.

(57) ABSTRACT

The present invention relates to *Labisia pumila* extract composition for reducing the progression of health problems and process for preparation thereof and their uses. More particularly, the present invention relates to corresponding process and to certain novel compounds of *Labisia pumila* extract composition for pharmaceutical formulation. One of the advantages of process of the extraction is having shorter duration extraction compared to the prior art documents. In addition, the *Labisia pumila* extract can be stored up to 3 years shelf-life with improved stability in storage, including shelf-life and their useable administration. Another advantage of the pharmaceutical formulation of the present invention is an improved formulation with pharmaceutical grade safety standard, and its optimised and stable pharmaceutical dosage form for clinical use and reducing the progression of health problems selected from obesity, metabolic syndrome, anti-inflammatory and anti-oxidant treatment.

5 Claims, 9 Drawing Sheets

| Details of Production Process for SKF7™ Extract |||| 
| Process | Step | Method | Materials |
| --- | --- | --- | --- |
| Raw Material Processing | Incoming assessment and washing | • Check plant quality<br>• Sort plants (leaves, stems, roots)<br>• Wash plants | • Water |
| | Drying | • Arrange plants in solar house<br>• Dry until reach required moisture (6 to 8%) | • Solar house |
| | Grinding | • Plants ground until desired size obtained<br>• Final quality control of raw material | • Grinder |
| | Packaging and storage | • Material packaged and labeled<br>• Stored under ambient conditions (RH 75 ± 5%, < 30°C) until further processing | • Foil bag |
| Extraction | Extraction Cycle 1 | • 1:1 water and ethanol added to extraction chamber with dried plant matter<br>• Extraction at 60 to 100°C for 2 to 6 hour<br>• Liquid extract removed for concentration ("extract 1")<br>• Extract residue left in chamber for Cycle 2 | • Water<br>• Ethanol<br>• Extraction chamber |
| | Extraction Cycle 2 | • Extract reside mixed with fresh water and ethanol (1:1)<br>• Extraction at 60 to 100°C for 2 to 6 hour<br>• Liquid extract removed for concentration ("extract 2")<br>• Extract residue discarded | • Water<br>• Ethanol<br>• Extraction chamber |
| Concentration | Concentration Cycle 1 | • Extract 1 placed in concentration chamber<br>• Temp: 80°C<br>• Pressure: 0.02 MPa<br>• Concentrate removed for mixing | • Concentration chamber<br>• Storage tank |
| | Concentration Cycle 2 | • Extract 2 placed in concentration chamber<br>• Temp: 80°C<br>• Pressure: 0.02 MPa<br>• Concentrate removed for mixing | • Concentration chamber<br>• Storage tank |
| | Mixing | • Concentrates 1 and 2 mixed | • Storage tank |
| Spray Drying | Homogenization | • Concentrate mixed with maltodextrin until homogeneous | • Homogenizer<br>• Maltodextrin |
| | Spray Drying | • Inlet Temperature = 150-170°C<br>• Outlet Temperature = 80-110°C<br>• Feed pump flow rate = 35-50 RPM | • Spray dryer |
| Packaging | | • Double packaged in plastic then aluminum bags<br>• Stored at ≤ 30 °C | • Ziploc plastic bag<br>• Aluminum moisture barrier bag |

RH: relative humidity; RPM: rotations per minute; MPa: megapascal.

FIGURE 3

| Chemical Class | Specific Phytochemical(s) |
|---|---|
| Flavonols | Myricetin |
| | Quercetin |
| | Rutin |
| Flavanols | Catechin |
| | Epigallocatechin |
| Flavanones | Naringenin |
| Flavones | Apigenin |
| Hydroxybenzoic acids | Gallic acid, methyl gallate |
| | Protocatechuic acid |
| | Salicylic acid |
| | Syringic acid |
| | Vanillic acid |
| Hydroxycinnamic Acids | Caffeic acid |
| | $m$-coumaric acid |
| Phenolic Alcohols | Pyrogallol |
| Organic Acids | Fumaric acid |
| | Succinic acid |
| Vitamins and Vitamin Precursors | Ascorbic acid |
| Saponins | Ardisiacrispin A |
| | Ardisicrenoside A |
| Alkylphenols | Irisresorcinol |
| Fatty Acids | α-linolenic acid |
| | Linoleic acid |
| | Oleic acid |
| | Palmitic acid |
| | Stearic acid |
| All compounds were detected in all three lots analyzed. ||

LABISIA PUMILA EXTRACT COMPOSITION AND ITS PHARMACEUTICAL FORMULATION

FIELD OF THE INVENTION

The present invention relates to *Labisia pumila* extract composition and its pharmaceutical formulation for reducing the progression of health problems and for the treatment of diseases and process for preparation thereof and their uses as pharmaceutical and nutraceutical bioactive that treats metabolic syndrome, inflammatory diseases, and hormonal imbalances. More particularly, the present invention relates to corresponding process and to certain novel *Labisia pumila* extract composition with pharmaceutical grade safety standard and its optimised and stable pharmaceutical dosage form for clinical use.

BACKGROUND OF THE INVENTION

*Labisia pumila* is an herbaceous plant found in the lowlands and forests of Southeast Asia, particularly Malaysia, Indonesia, Thailand, Laos, Cambodia, and Vietnam. It is a slow growing plant and propagates by its rhizomes, leaves, and seeds. The plant grows wild at 80-100 meters above sea level but can also be cultivated. *Labisia pumila* is believed to have phytoestrogen acting as primary female sex hormone, particularly estrogen. This is because the plant is widely used as woman post-partum medicine traditionally (Abdullah et al., 2013). There is now an increasing demand for the supply of "kacip fatimah' (*Labisia pumila* syn. *Labisia pothoina*) in the food industries, the reproducibility of extraction processes is still in doubt due to the lack of reliable chemical profiling methods.

Prior art U.S. Pat. No. 7,879,368 disclosed a process for preparation of *Labisia pumila* extract by extracting dried *Labisia pumila* plant material with water at a ratio of 1:6 of dried *Labisia pumila* plant material:water to form a water-soluble extract and drying the extract wherein the extracting is carried out at 80° C. for 3 hours and with continuous stirring. Optionally wherein the extraction process is repeated and the ratio of *Labisia pumila* plant material:water is 1:6; optionally wherein the *Labisia pumila* extract is dried and concentrated by spray-drying; optionally wherein the spray-drying is performed using a spray tower having a tower inlet and outlet, and wherein tower inlet temperature is 185° C. and wherein tower outlet temperature is 107° C., respectively.

Meanwhile another prior art, U.S. Pat. No. 9,358,260 disclosed a process for obtaining a *Labisia pumila* extract comprising the steps of obtaining an extract from dried *Labisia pumila* plant material using water extraction, filtering the extract to obtain filtrate and *Labisia pumila* plant material residue, re-extracting the *Labisia pumila* residue using water extraction, centrifuging the *Labisia pumila* extracts to obtain a supernatant, characterized in that the *Labisia pumila* plant material includes leaves and roots in a ratio of 3:2 by weight and ratio of the dried plant material to water used in the water extraction process is 1:10 by weight. The process for obtaining a *Labisia pumila* extract, the dried *Labisia pumila* plant material is extracted through water extraction using distilled water or reverse osmosis water or deionised water, wherein the water is used as a solvent during the extraction process to produce higher quality of extract. The quantity ratio of dried plant material to the solvent is preferably one part of dried plant material to ten parts of solvent. In a preferred embodiment of the process for obtaining a *Labisia pumila* extract, the water extraction is performed at a temperature of 80° C. for three hours with stirring to obtain uniform extract. In the next step, the extract is filtered to obtain filtrate and *Labisia pumila* plant material residue. The *Labisia pumila* residue is re-extracted using water extraction. In a preferred embodiment, the residue is re-extracted with the same volume of water used in the initial extraction and re-extracted at a temperature of 80° C. for an hour with stirring. The *Labisia pumila* extracts is then centrifuged to obtain the supernatant. In a preferred embodiment of the process for obtaining a *Labisia pumila* extract, the centrifuging is conducted at 3500 rpm for 15 minutes. In a preferred embodiment of the process for obtaining a *Labisia pumila* extract, the supernatant is further filtered and concentrated using rotary evaporator at temperature of 75° C. to evaporate the excessive solvent from the supernatant. The supernatant is filtered using Buchner Funnel. In a preferred embodiment of the process for obtaining a *Labisia pumila* extract, the supernatant is freeze-dried to obtain powdery residue. The supernatant is transferred into a freeze dryer vessel and frozen in a freezer at −20° C. The frozen extract is then dried in a freeze dryer until a powdery residue is obtained.

WO2013112040A1 disclosed the a method for producing a plant extract formulation according to claim 7, comprising the following steps: (i) providing a plant or a part of a plant of the family Myrsinaceae, preferably from the genus *Labisia*, more preferably from *Labisia pumila*, particularly preferably from the roots of *Labisia pumila*, (i-a) optionally drying the plant or a part of a plant of step (i), (ii) extraction of said plant or a part of a plant provided in step (i) or (i-a) with a mixture of water and an alcohol having 1 to 3 carbon atoms, preferably with a mixture of ethanol and water, wherein the volume ratio (v/v) of said alcohol:water in the range of 1:2 to 30:1, more preferably in the range of 1:1 to 25:1, most preferably in the range of 3:2 to 20:1, (ii-a) optionally partially or fully removing the alcohol having 1 to 3 carbon atoms of step (ii), preferably at a temperature below 70° C., more preferably in the range from 15 to 55° C., (iii) mixing the extract obtained in step (ii) or (ii-a) with one or more solid carrier substances, preferably one or more solid carrier substances selected from the group consisting of maltodextrins, silica, talc, lactose, dextrose, sucrose, sorbitol, mannitol, starches, gum acacia, calcium phosphate, orally acceptable stearate salts, preferably magnesium stearate, alginates, tragacanth, gelatins, calcium silicates, cellulose and cellulose derivatives, preferably microcrystalline cellulose or methyl cellulose, polyvinylpyrrolidones, and propylhydroxybenzoates, (iv) optionally drying the mixture obtained in step (iii), preferably by spray-drying or freeze-drying.

Another prior art, WO2016093692A1 disclosed a process to obtain an extract of *Labisia pumila* comprising: i. obtaining a *Labisia pumila* plant sample; ii. reducing the water content of the plant sample to provide a dried sample; iii. subjecting the dried sample to extraction with a solvent containing a mixture of an alcohol and water to provide an alcoholic extract; and iv. removing the solvent from the alcoholic extract to obtain the extract of *Labisia pumila*. The plant sample may be derived from the leaves of a *Labisia pumila* plant, optionally the plant sample may be additionally or alternatively derived from the roots and/or stems of a *Labisia pumila* plant. In further embodiments, reducing the water content in step (ii) is performed for from 24 hours to 72 hours at from 40° C. to 60° C. For example, reducing the water content can be performed for 72 hours at 55° C. In certain embodiments, the dried sample is ground into a powder before use in step (iii). In yet further embodiments, extraction step (iii) may comprise the use of a soxhlet extracting technique. The solvent containing a mixture of an alcohol and water is replaced at least once to form at least two alcoholic extracts that are combined together. In yet further embodiments, extraction step (iii) may be performed for from 5 hours to 240 hours. For example, the extraction step is performed for 120 hours. The solution containing a mixture of an alcohol and water may have a volumetric ratio (alcohol:water) of from 4:1 to 1:4 (e.g. the volumetric ratio may be 1:1). In yet still further embodiments, the step of removing the solvent from the alcoholic extract in step (iv) may be performed by spray drying, freeze drying or evaporation.

Accordingly, it can be seen from the prior art that there is a need to provide an optimized extraction process of *Labisia pumila* plants that will give optimised stability, higher yield, quality, safety and efficacy of the *Labisia pumila* extract, and also an optimized pharmaceutical dosage formulation that are stable, safe and efficacious for clinical use.

*Labisia pumila* is typically boiled and the water-soluble extract is taken as a drink. While it is most extensively used during childbirth and the postpartum period, *Labisia pumila* is used by both men and women for a variety of other conditions. There is no documentation in the literature regarding the recommended or practical frequency or dose of use in any population. *Labisia pumila* is widely available in Malaysia in supplements, traditional medicines, teas, and cosmetic products, but the overall use level is not well documented. It also cannot be determined from publicly available information how much *Labisia pumila* extract is contained in each product nor at what level individual chemical components are present in these extracts.

WO2013112040A1 disclosed the *Labisia pumila* extracts is used for the cosmetic prevention, treatment or reduction of cellulite, and/or for the non-therapeutic, preferably cosmetic, reduction of the lipid quantity contained in subcutaneous fat tissue, and/or inhibition of the differentiation of preadipocytes, and/or inhibition of the lipogenesis in adipocytes, and/or as cosmetic anti-cellulite active. Plant extract formulation, preferably in solid form, obtainable from a plant of the family Myrsinaceae, preferably from the genus *Labisia*, more preferably from *Labisia pumila*, particularly preferably from the roots of *Labisia pumila*, comprising (a) one or more compounds of formula (I) as defined in claim 5 or a physiologically acceptable salt thereof in a total amount effective, preferably the total amount being in the range from 0.1 to 15 wt. %, more preferably from 0.2 to 10 wt. %, particularly preferably from 0.5 to 6 wt. %, most preferably from 1 to 5 wt. %, most preferably from 1.25 to 4 wt. %, based on the total weight of the plant extract formulation, (b) one or more further substances naturally occurring in said plant from, wherein said one or more further substances are not compounds of formula (I) as defined in claim 5 or a physiologically acceptable salt thereof, and (c) one or more solid carrier substances, preferably one or more solid carrier substances selected from the group consisting of maltodextrins, silica, talc, lactose, dextrose, sucrose, sorbitol, mannitol, starches, gum acacia, calcium phosphate, orally acceptable stearate salts, preferably magnesium stearate, alginates, tragacanth, gelatins, calcium silicates, cellulose and cellulose derivatives, preferably microcrystalline cellulose or methyl cellulose, polyvinylpyrrolidones, and propylhydroxybenzoates.

While, the prior art WO2016093692A1 disclosed a pharmaceutical formulation comprising an extract of *Labisia pumila* and/or a nano-formulated liposome extract of *Labisia pumila* in admixture with a pharmaceutically acceptable adjuvant, diluent or carrier for use in the manufacture of a medicament for the treatment of obesity. WO2009116848A1 revealed that the use of standardised aqueous extract of *Labisia pumila* in orally sufficient amount characterised in that said extract reduces the risk or progression of cardiovascular diseases and age-related health problems wherein the amount of extract orally taken ranges from 100-500 mg/day. The extract influences pathophysiological changes, including regulation of genes associated with insulin resistance, obesity, metabolic syndrome, diabetes and aging. However, it is unclear the main phytochemical components extracted from *Labisia pumila* which contributed to each medical treatment.

In view of the above shortcomings, the present invention aims to provide new *Labisia pumila* extract composition for reducing the progression of health problems and diseases and an improvement process for preparation thereof and their uses. In addition, the present invention discloses an improvement novel compound of *Labisia pumila* extract composition for pharmaceutical formulation and dosage form with improved stability in storage, including shelf-life and their useable, efficacious and safe administration for clinical use.

SUMMARY OF THE INVENTION

The present invention provides a process for obtaining a *Labisia pumila* extract composition comprising the steps of: extracting dried *Labisia pumila* plant of material with a solvent at a ratio of between 1:5 to 1:20-respectively in weight/volume at a temperature of 60-100° C. for 2-6 hours in an extraction chamber to obtain a first extract; filtering the first extract to obtain a first filtrate and a plant residue; re-extracting the plant residue with the solvent at a temperature of 60-100° C. for 2-6 hours in the extraction chamber to obtain a second extract; filtering the second extract to obtain a second filtrate and the plant residue; concentrating the first extract and the second extract; mixing the first concentrated extract and the second concentrated extract to form the *Labisia pumila* extract; homogenizing the *Labisia pumila* extract with maldodextrins into the *Labisia pumila* extract composition; and spray-drying the *Labisia pumila* extract composition.

In another embodiment of the present invention, the dried *Labisia pumila* plant of material is prepared by the following steps
  (i) drying leaves of the *Labisia pumila* plant at 40-55° C. until a moisture content is 6-8%;
  (ii) drying stems and roots of the *Labisia pumila* plant at 40-55° C. until a moisture content is 6-8%;
  (iii) grounding the dried leaves, stems and roots of the *Labisia pumila* plant to a particle size of 2-4 mm.

In yet another embodiment of the present invention, the solvent is water and ethanol at a volumetric ratio of 1:1.

In yet another embodiment of the present invention, the concentrating for the first extract is performed at a temperature of 80° C., pressure at 0.02 MPa in a concentration chamber.

In another embodiment of the present invention, the concentrating for the second extract is performed at a temperature of 80° C., pressure at 0.02 MPa for in a concentration chamber.

In yet another embodiment of the present invention, the spray-drying is performed at an inlet temperature of 150-170° C. and an outlet temperature of 80-110° C. with a feed pump flow rate of 35-50 RPM.

Figure 4:
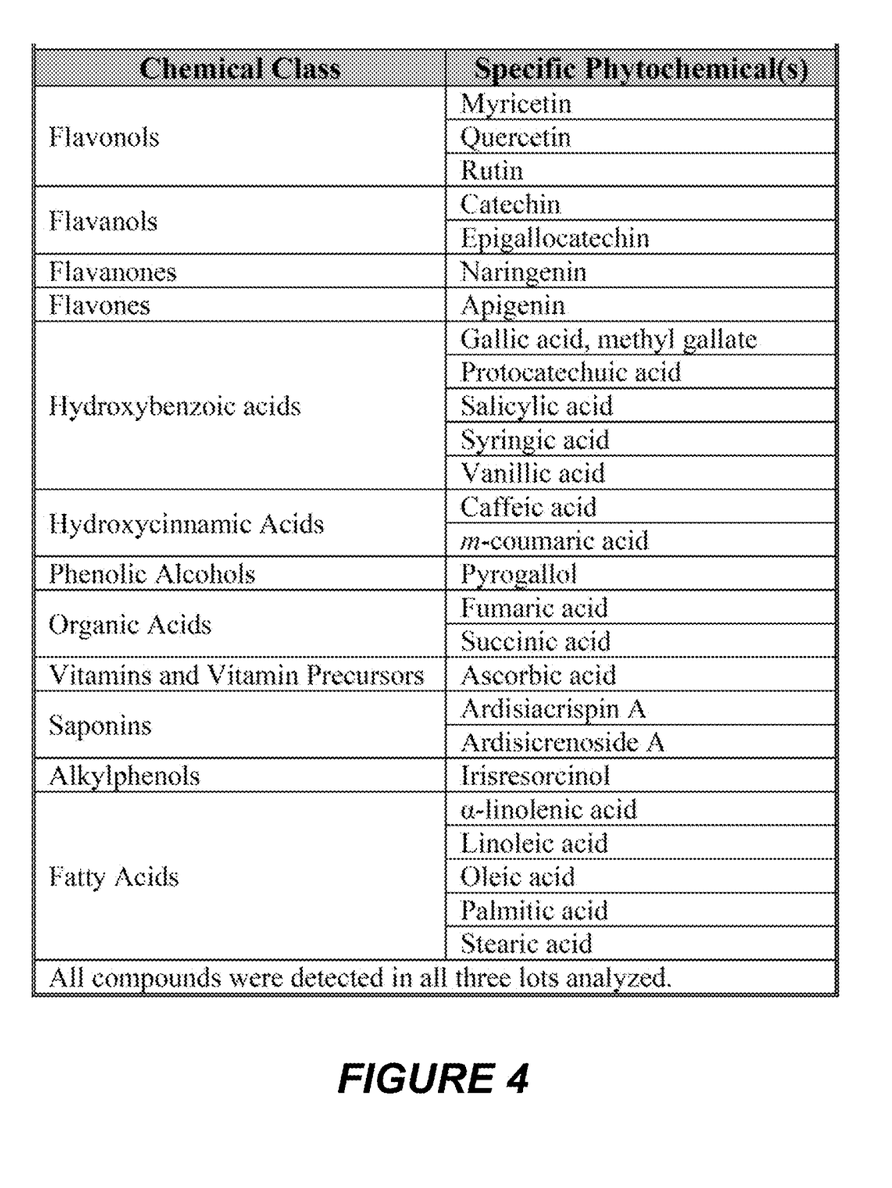
FIG. 4 illustrates phytochemicals positively identified in SKF7™ extract using LC-MS/MS in accordance of the present invention.
Figure 6:
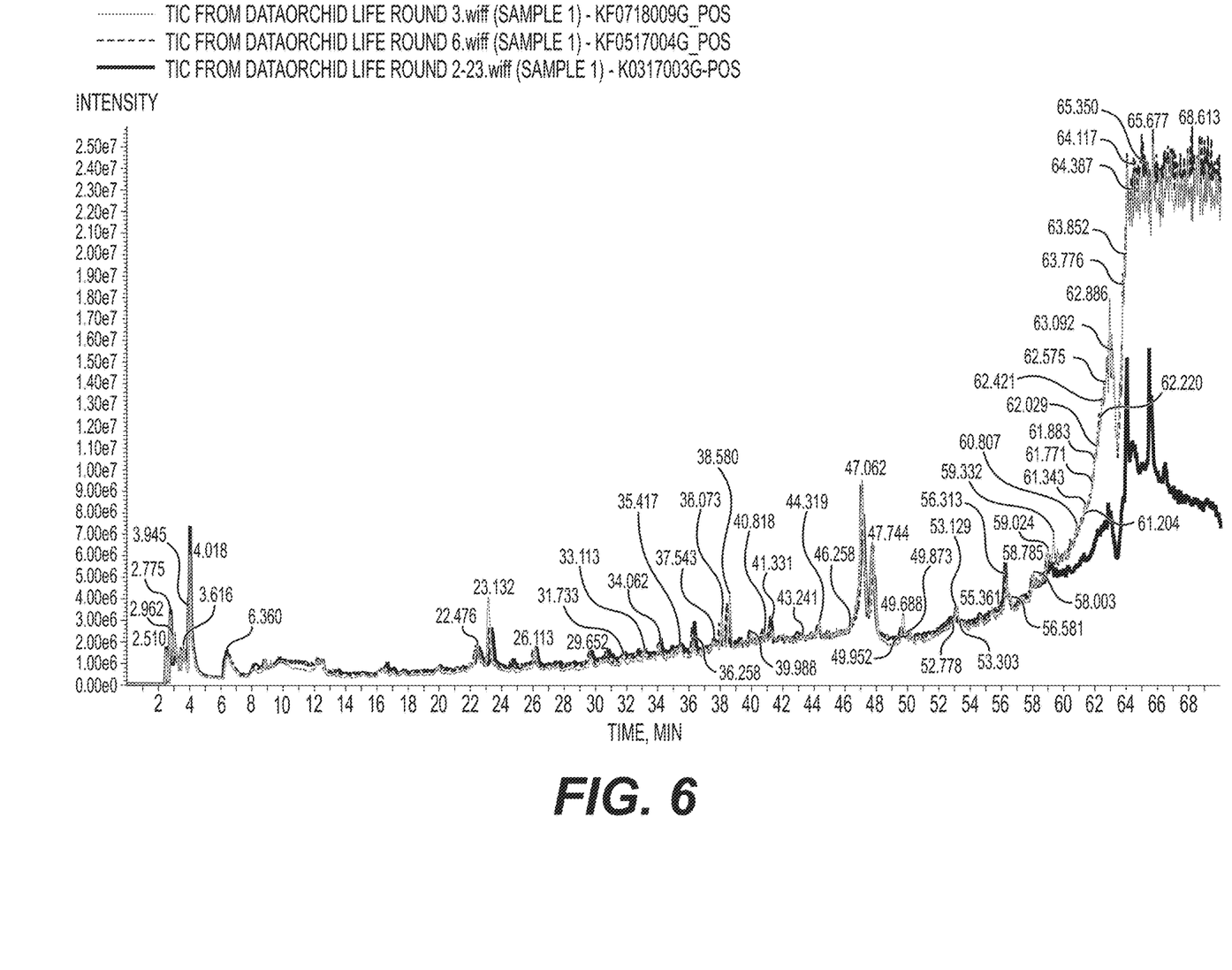
FIG. 6 illustrates overlay of SKF7™ LC-MS/MS Chromatograms in positive ion mode in accordance of the present invention.

*Labisia pumila* extract composition obtainable from the process of the present invention is *Labisia pumila* aqueous ethanolic extract. A *Labisia pumila* extract composition characterized in that it produces 27 peaks in positive ion mode when subjected to LC-MS/MS chromatography and produces 27 peaks in negative ion mode when subjected to LC-MS/MS chromatography. These 27 constituents were positively identified in LC-MS/MS chromatography, including various flavonoids, phenolic acids, and fatty acids (FIG. 4). The chemical fingerprints showing the overall composition of this complex botanical extract are shown in FIG. 6 (positive ionization mode) and FIG. 7 (negative ionization mode).

Standardised *Labisia pumila* aqueous ethanolic extract in orally effective amount characterised in that said extract for reducing the progression of problems selected from obesity. In another embodiment of the present invention, standardised *Labisia pumila* aqueous ethanolic extract for use wherein the effective and safe amount of extract orally taken ranges from 180 mg/day to 1500 mg/day for a period of between 7 days to more than 12 months. In another embodiment of the present invention, standardized *Labisia pumila* aqueous ethanolic extract for use wherein the extract reduces the progression of health problems selected from obesity in humans. In yet another embodiment of the present invention, standardized *Labisia pumila* aqueous ethanolic extract for use wherein the extract reduces the progression of health problems selected from obesity, metabolic syndrome, anti-inflammatory and antioxidant treatment.

A *Labisia pumila* extract comprises one or more extract components of flavonols; flavanols; flavanones; flavones; hydroxybenzoic acids; hydroxycinnamic acids; phenolic alcohols; organic acids; vitamins and vitamin precursors; saponins; alkylphenols; and fatty acids. In one of the embodiments of the present invention, the flavonols comprises myricetin, quercetin and rutin. In another embodiment of the present invention, the flavanols comprises catechin and epigallocatechin. In yet another embodiment of the present invention, the flavanones comprises naringenin. In another embodiment of the present invention, the flavones comprises apigenin. In another embodiment of the present invention, wherein the hydroxybenzoic acids comprises methyl gallate, protocatechuic acid, salicylic acid, syringic acid and vanillic acid. In yet another embodiment of the present invention, the hydroxycinnamic acids comprises caffeic acid and m-coumaric acid. In yet another embodiment of the present invention, the phenolic alcohols comprises pyrogallol. In another embodiment of the present invention, the organic acids comprises fumaric acid and succinic acid. In yet another embodiment of the present invention, the vitamins and vitamin precursors comprise ascorbic acid. In another embodiment of the present invention, the saponins comprises ardisiacrispin A and ardisicrenoside A. In another embodiment of the present invention, wherein the alkylphenols comprises irisresorcinol and the fatty acids comprises α-linolenic acid, linoleic acid, oleic acid, palmitic acid and stearic acid. The *Labisia pumila* extract further having antioxidant properties of 65-92% of 1,1-diphenyl-2-picrylhydrazyl (DPPH) radical scavenging activity and the average total phenolic content (TPC) was more than 100 mg gallic acid equivalents (GAE)/g.

A pharmaceutical formulation comprising a *Labisia pumila* extract in admixture with a pharmaceutically acceptable carrier for reducing the progression of health problems selected from obesity. In one of the embodiments of the present invention, the pharmaceutical formulation wherein the acceptable carrier is maltodextrins and other excipients.

In yet another embodiment of the present invention, the *Labisia pumila* extract is a *Labisia pumila* aqueous ethanolic extract. The pharmaceutical formulation is formulated as an oral effective dose for acceptable daily intake of 180 mg/day to 1500 mg. A delivery system for orally administering the pharmaceutical formulation wherein the delivery system comprises tablets, capsules, pills, granules, syrups, powders, concentrates or dry syrups.

One of the advantages of process of the extraction is having shorter duration extraction compared to the prior art documents. In addition, the *Labisia pumila* extract can be stored at least 3 years shelf-life with improved stability in storage, including shelf-life and their useable administration. Another advantage of the pharmaceutical formulation of the present invention is an improved formulation with pharmaceutical grade safety standard, and its optimised and stable pharmaceutical dosage form for clinical use and for obesity, metabolic syndrome, anti-inflammatory, treatment from 180 mg/day to 1500 mg/day for a period of 7 days to more than 12 months.

Another advantage of the method of the present invention is that
a. ghrelin levels were significantly reduced in animals treated with *Labisia pumila* extract composition 77.5 mg/kg, SKF7™ 155 mg/kg, *Labisia pumila* extract composition 310 mg/kg groups as compared to DIO control group by 18.0% ($P \leq 0.05$), 44.5% ($P \leq 0.01$), 39.5% ($P \leq 0.01$) and, respectively. Weight loss induce significant increases in the concentration of ghrelin, a potent orexigenic hormone. Elevations in ghrelin concentration, either endogenous or exogenous, are associated with feelings of hunger and increased food intake. Interestingly, *Labisia pumila* extract composition inhibits ghrelin production levels while inducing weight loss. Hence, no significant changes were observed in average daily feed consumption in all groups.
b. Proven safe in subchronic and chronic toxicology studies (and other toxicology studies).

Further advantages of the system in accordance with the invention and its application can be derived from the description and the accompanying drawings. The above-mentioned features and those to be further described below can be utilized in accordance with the invention individually or collectively in arbitrary combination.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3 illustrate steps, methods, and materials, used in the production of SKF7™ in accordance of the present invention.

DETAILED DESCRIPTIONS OF THE INVENTION

The present invention will now be described in detail in connection with specific embodiments with reference to the accompanying drawings. Unless the context requires otherwise, throughout the specification and claims which follow, the word "comprise" and variations thereof, such as, "comprises" and "comprising" are to be construed in an open, inclusive sense that is as "including, but not limited to". Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, terms such as "first," "second," "third," etc., merely identify one of several portions, components and/or points of reference as disclosed herein, and do not limit the present invention to any particular configuration or orientation.

The term "shelf life" refers to the amount of time the pharmaceutical composition may be stored without loss of potency and/or performance profile.

By the term "extract", either a direct extract (in liquid or preferably dried form), e.g. obtained as described below, or preferably a further enriched extract (obtainable e.g. by one or more further purification steps after extraction, e.g. chromatography, for example as described below) containing one or more, preferably two or more compounds.

"Obtainable" means that a product (e.g. extract or compound) may be obtained by a certain method, and preferably is obtained by said process.

By "administered" or "administering" herein is meant administration of a prophylactically and/or therapeutically effective dose of a compound of *Labisia pumila* extract or a mixture of compounds of *Labisia pumila* extract, or an extract comprising one or more the compounds of *Labisia pumila* extract, to a human being in need of such treatment.

By "effective amount" or "effective dose" herein is meant an amount or a dose that produces the (therapeutic or cosmetic) effect for which it is administered.

The term "SKF7™" used throughout the entire patent specification is a tradename of *Labisia pumila* extract composition either a direct extract (in liquid or preferably dried form), e.g. obtained as described below, or preferably a further enriched extract (obtainable e.g. by one or more further purification steps after extraction, e.g. chromatography, for example as described below) containing one or more, preferably two or more compounds.

The present invention relates to corresponding process and to certain novel compounds of *Labisia pumila* extract composition for pharmaceutical formulation. Prior to preparation of the *Labisia pumila* extract, the dried *Labisia pumila* plant of material of the present invention is prepared by the following steps (i) drying leaves of the *Labisia pumila* plant at 40-55° C. for 5 hours until a moisture content is 6-8%;

(ii) drying stems and roots of the *Labisia pumila* plant at 40-55° C. for 6 hours until a moisture content is 6-8%; and (iii) grounding the dried leaves, stems and roots of the *Labisia pumila* plant to a particle size of 2-4 mm.

The present invention is further explained by the following examples. The specific examples which follow illustrate the methods in which the compositions of the present invention may be prepared, components therein and their use, as well as other embodiments of the invention, but are not to be construed as limiting the invention in scope.

Example 1

Figure 1:
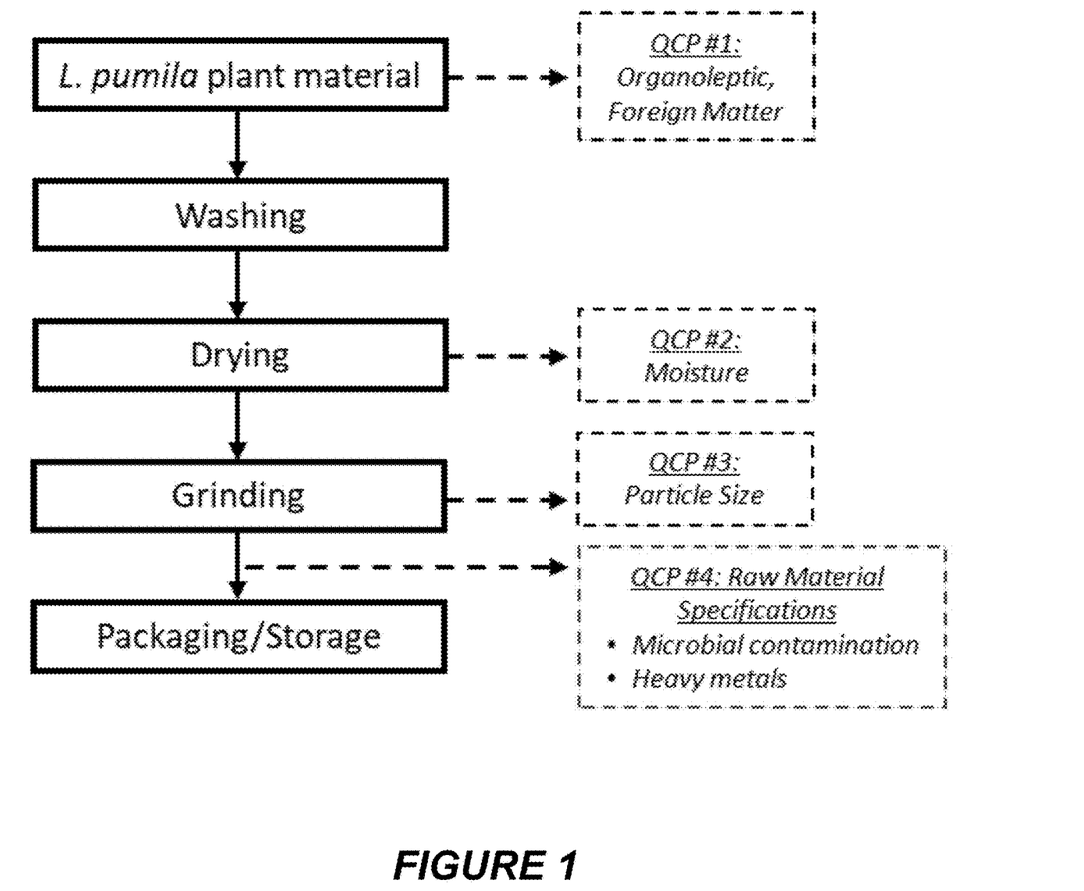
FIG. 1 illustrates processing steps and quality control parameters (QCPs) for *Labisia pumila* raw plant material in accordance of the present invention.

Prior to extraction, the selected *Labisia pumila* plant material was examined for appearance, organoleptic characteristics, and the presence of foreign matter. After the initial assessment, the plants were sorted (leaves, stems, roots) and washed with water. Plants were then arranged by hand in a drying oven. Drying is performed at 40-55° C. (stems and roots). The resulting moisture content was 6-8%. Dried plants were grounded to a final particle size of 2-4 mm. Ground plant materials was tested for moisture level, heavy metals, and general microbial contaminants as shown in FIG. 1. Materials fulfil all specifications were labelled and stored under ambient conditions (75% relative humidity, <30° C.) until further processing. Storage was performed for no longer than one week.

A process for obtaining a *Labisia pumila* extract composition comprising the steps of:

(i) extracting dried *Labisia pumila* plant of material with a solvent at ratio of 1:5 to 1:20 respectively in weight/volume at a temperature of 60-100° C. for 2-6 hours in an extraction chamber to obtain a first extract;

(ii) filtering the first extract to obtain a first filtrate and a plant residue;

(iii) re-extracting the plant residue with the solvent at a temperature of 60-100° C. for 2-6 hours in the extraction chamber to obtain a second extract;

(iv) filtering the second extract to obtain a second filtrate and the plant residue;

(v) concentrating the first extract and the second extract;

(vi) mixing the first concentrated extract and the second concentrated extract to form the *Labisia pumila* extract;
(vii) homogenizing the *Labisia pumila* extract with maldodextrins into the *Labisia pumila* extract composition; and
(viii) spray-drying the *Labisia pumila* extract composition.

The solvent used in the present invention is water and ethanol at a volumetric ratio of 1:1. The concentrating for the first extract is performed at a temperature of 80° C., pressure at 0.02 MPa in a concentration chamber. In another embodiment of the present invention, the concentrating for the second extract is performed at a temperature of 80° C., pressure at 0.02 MPa for in a concentration chamber. The spray-drying is performed at an inlet temperature of 150-170° C. ° C. and an outlet temperature of 80-110° C. with a feed pump flow rate of 35-50 RPM.

The *Labisia pumila* extract composition obtainable from the process of the present invention is *Labisia pumila* aqueous ethanolic extract.

The present invention is further explained by the following examples. The specific examples which follow illustrate the methods in which the compositions of the present invention may be prepared, components therein and their use, as well as other embodiments of the invention, but are not to be construed as limiting the invention in scope.

Example 2

Figure 2:
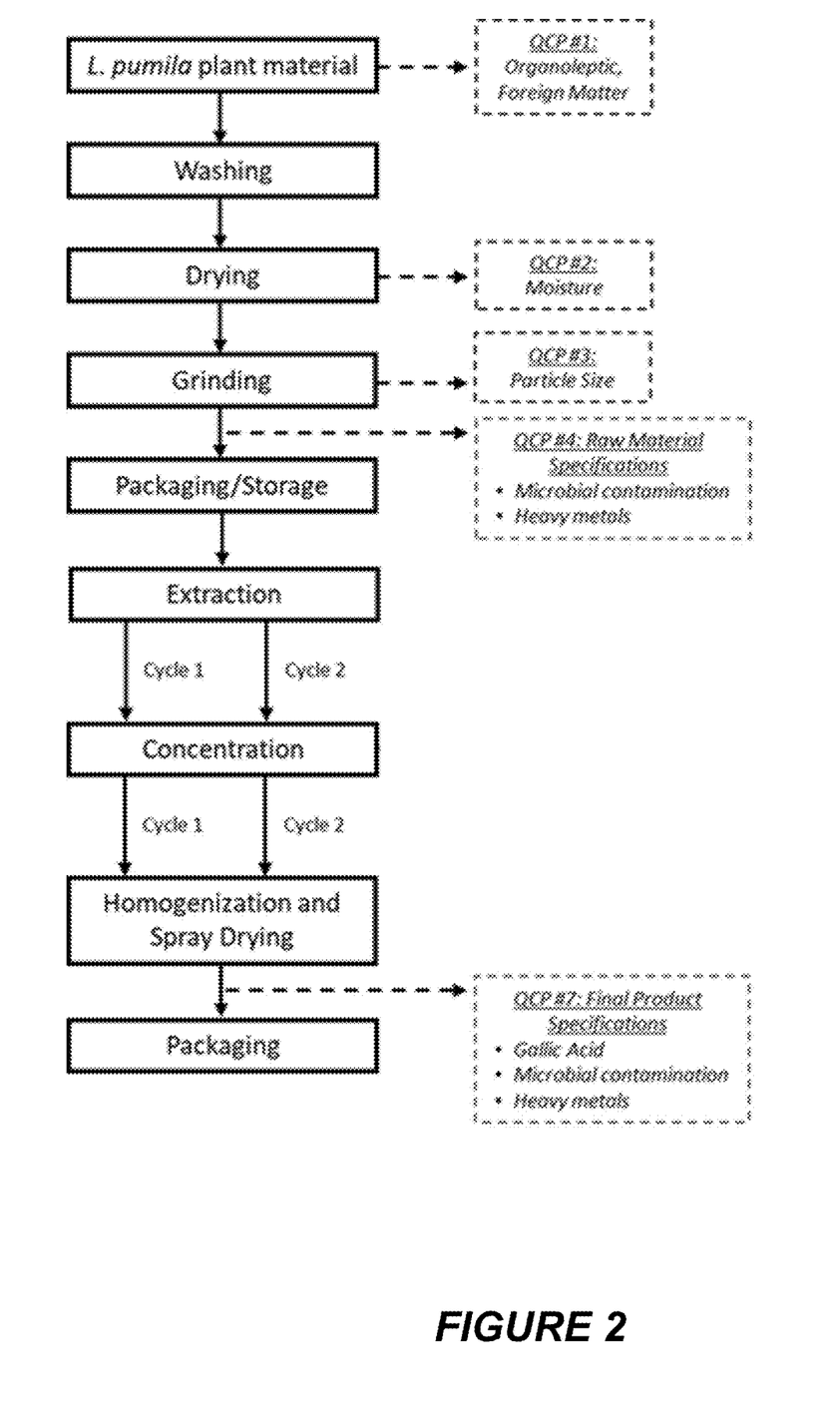
FIG. 2 illustrates manufacturing process and quality control parameters (QCPs) to produce SKF7™ extract in accordance of the present invention.

The extraction process was performed at an extraction plant. *Labisia pumila* extract composition of the present invention was labelled as SKF7™ and produced in accordance with current Good Manufacturing Practices (cGMP). A general flow chart of the production process for SKF7™ extract is shown in FIG. 2. Extraction was performed using a 1:1 mixture of water and ethanol as the solvent. The water used for extraction was filtered and deionized. *L. pumila* whole parts or a combination of stems, leaves and/or roots were used. Ten parts solvent mixture and 1 part plant material (v/w) were placed in the extraction chamber. Extraction proceeds for 5 hours at 80° C. After this cycle, the liquid extract (Extract 1) was separated from the plant residue by filtration and sent to the concentration chamber. Fresh solvent was added to the extraction residue and another extraction cycle (5 hours at 80° C.) was performed. The resulting extract (Extract 2) was separated from the plant residue by filtration and sent for concentration. The remaining residue was discarded.

Extract 1 was used in the first concentration cycle. Concentration proceeds at 80° C. under 0.02 MPa pressure, for 50 minutes (Concentrate 1). Concentrate 1 was then moved to the storage tank and held at 4° C. until mixing. Extract 2 was added to the chamber and concentrated at 80° C. under 0.02 MPa pressure, for 80 minutes (Concentrate 2). Once both extracts had been concentrated, they were mixed. The combined liquid concentrate was mixed with maltodextrin powder using a homogenizer until homogeneous. The mixture was then spray dried, and the dried extract collected from the chamber. Final quality control testing was performed on the spray dried extract and includes particle size, moisture, residual alcohol, gallic acid and/or other compounds, pesticides, heavy metals, and microbial contamination and other toxins or contaminants. The steps, methods, and materials used in the production of SKF7™ were described in FIG. 3. Final products were packaged and stored at 15-25° C. for up to 3 years for manufacturing of the final commercial product. To ensure a consistent product, each batch of SKF7™ is evaluated against an established set of specifications.

*Labisia pumila* is capable of synthesizing multiple nutrients, including vitamins, minerals, fatty acids, and amino acids. Many of these constituents are expected to be preserved in the extract. The extracts of *Labisia pumila* have been shown to contain a variety of phytochemicals. The *Labisia pumila* extract comprises one or more extract components of flavonols, flavanols, flavanones, flavones, hydroxybenzoic acids, hydroxycinnamic acids, phenolic alcohols, organic acids, vitamins and vitamin precursors, saponins, alkylphenols and fatty acids. The flavonols of the present invention comprises myricetin, quercetin and rutin. The flavanols comprises catechin and epigallocatechin. The flavanones comprises naringenin. Meanwhile, the flavones comprises apigenin. The hydroxybenzoic acids comprises methyl gallate, protocatechuic acid, salicylic acid, syringic acid and vanillic acid. The hydroxycinnamic acids comprises caffeic acid and m-coumaric acid. The phenolic alcohols comprises pyrogallol and the organic acids comprises fumaric acid and succinic acid. In addition, the vitamins and vitamin precursors comprise ascorbic acid. The saponins comprises ardisiacrispin A and ardisicrenoside A. The alkylphenols comprises irisresorcinol and wherein the fatty acids comprises α-linolenic acid, linoleic acid, oleic acid, palmitic acid and stearic acid. In another embodiment of the present invention, *Labisia pumila* extract further having antioxidant properties of 65-92% of 1,1-diphenyl-2-picrylhydrazyl (DPPH) radical scavenging activity and the average total phenolic content (TPC) was more than 100 mg gallic acid equivalents (GAE)/g.

The present invention is further explained by the following examples. The specific examples which follow illustrate the methods in which the compositions of the present invention may be prepared, components therein and their use, as well as other embodiments of the invention, but are not to be construed as limiting the invention in scope.

Example 3

Figure 5:
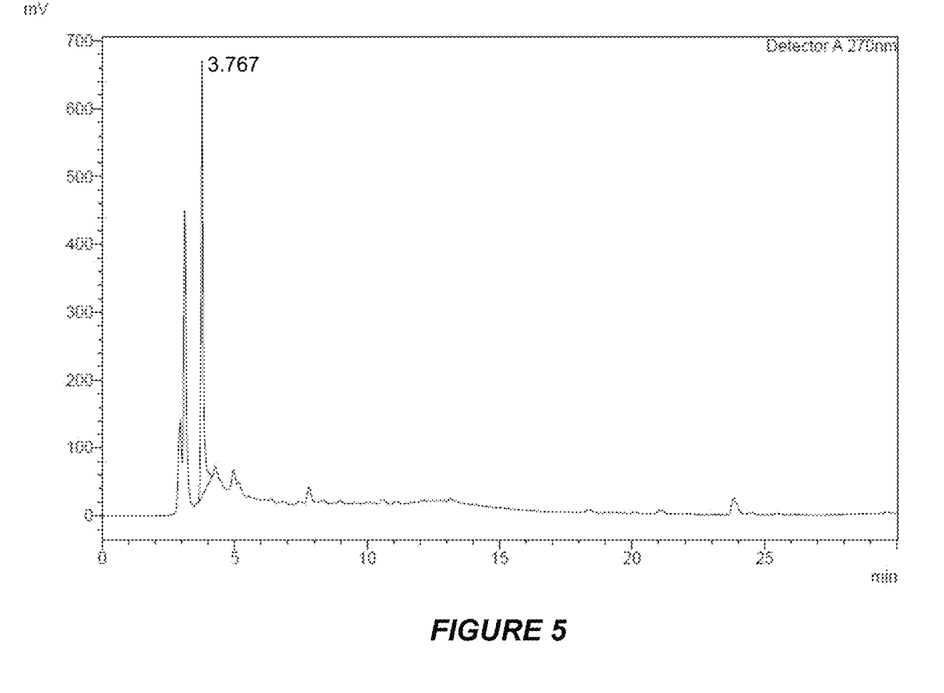
FIG. 5 illustrates SKF7 with Gallic Acid assay chromatogram and quantification (validated HPLC method, Retention time ~3.7 min) in accordance of the present invention.

Twenty-seven constituents were positively identified, including various flavonoids, phenolic acids, and fatty acids as shown in FIG. 4. A chromatogram of SKF7™ as shown in FIG. 5 with validated HPLC method was used in the Quality Control for estimation of Gallic Acid (Retention time ~3.7 min) in SKF7™.

Figure 7:
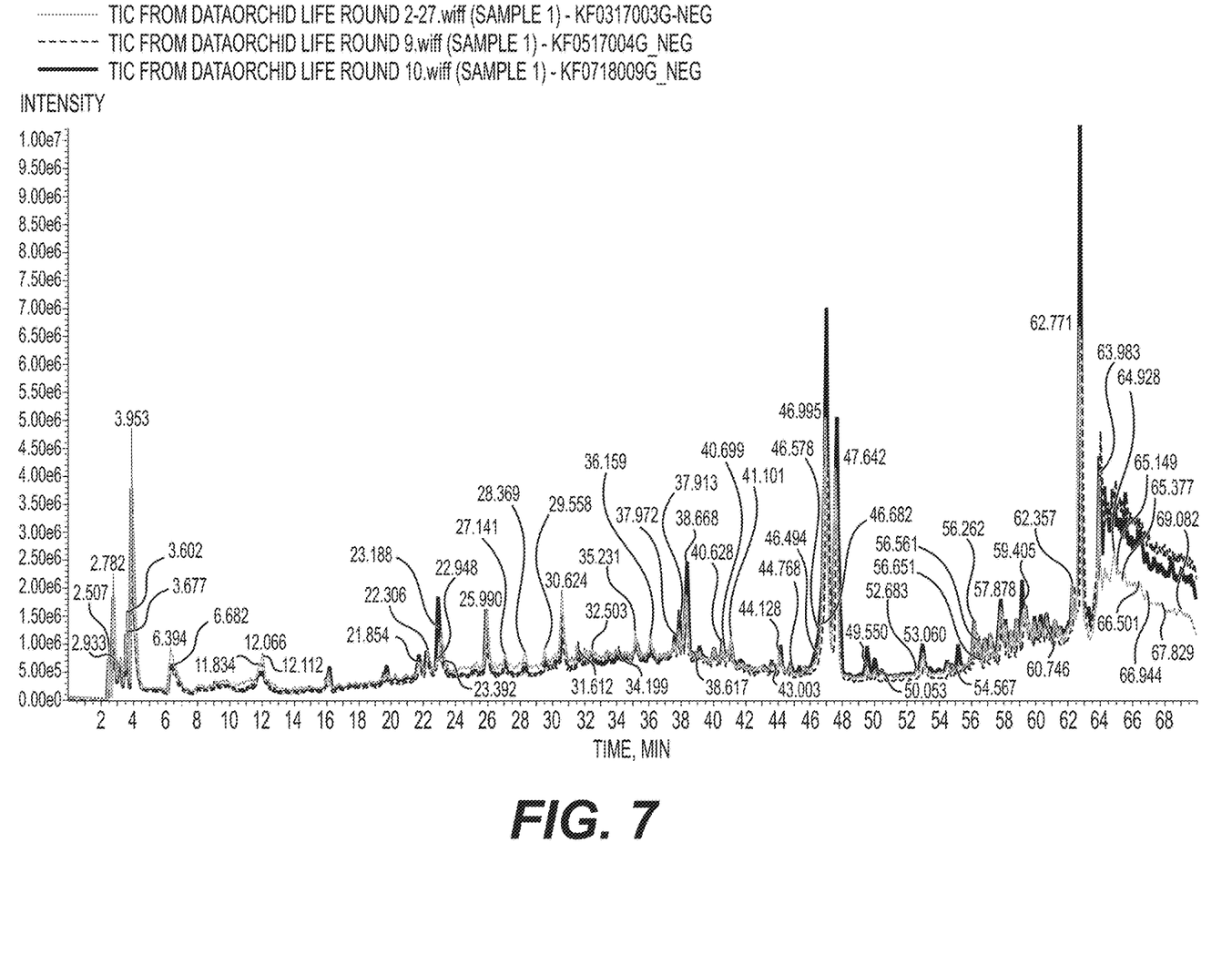
FIG. 7 illustrates overlay of SKF7™ LC-MS/MS Chromatograms in negative ion mode in accordance of the present invention.

Overlays are shown in FIG. 6 (positive ionization mode) and FIG. 7 (negative ionization mode). Overall, all three lots had similar peaks and peak intensities, indicating that the chemical composition of the extracts was very similar. The maintenance of the chemical fingerprint for each batch was provided to ensure compositional similarity and confirm that the batch of SKF7™ used in the pivotal toxicology studies presented as representative of commercial product that are safe and efficacious.

The average DPPH radical scavenging activity of SKF7™ (compared to ascorbic acid, set to 100%) was 65-92%. The average TPC of SKF7™ was more than 100 mg gallic acid equivalents (GAE)/g.

Pharmaceutical Manufacture and Formulation

Obesity is one of the main factors in the development of cardiovascular diseases. As a side effect the levels of cholesterol, blood pressure, blood sugar and uric acid in obese people are usually higher than those of persons of normal weight. The formulation according to the present invention has improved properties compared to other formulations existing in the art, as will be described below. A pharmaceutical formulation of the present invention comprising a *Labisia pumila* extract in admixture with a pharmaceutically acceptable carrier and excipients of the present invention for reducing the progression of health problems selected from obesity. The acceptable carrier and excipients of the present invention is maltodextrins and other excipients in the TABLE 1 below. The *Labisia pumila* extract for the pharmaceutical formulation is a *Labisia pumila* aqueous ethanolic extract. It is preferable that an oral effective dose for acceptable daily intake of 180 mg to 1500 mg per day. A delivery system for orally administering the pharmaceutical formulation of the present invention, wherein the delivery system comprises tablets, capsules, pills, granules, syrups, powders, concentrates or dry syrups. It is desired that the formulation essentially retains its physical and chemical stability, as well as its biological activity upon storage. The storage period is generally selected based on the intended shelf-life of the formulation.

In one embodiment of the present invention, *Labisia pumila* extract for the pharmaceutical formulation in CAPSULE FORMULATION: 320 mg capsule (Size 0)
  Active Ingredient: SKF7® (*Labisia pumila* Standardized Extract)
  Gallic Acid per capsule: 3.294 mg-4.456 mg per 320 mg capsule. (HPLC assay)
  Weight per Capsule: 320 mg (size 0)

In another application, a standardized *Labisia pumila* aqueous ethanolic extract for use to reduce the progression of age-related health problems selected from obesity in humans. Further application of the present invention, a standardized *Labisia pumila* aqueous ethanolic extract for use to regulate obesity and metabolic syndrome symptoms and parameters in humans.

The present invention is further explained by the following examples. The specific examples which follow illustrate the methods in which the compositions of the present invention may be prepared, components therein and their use, as well as other embodiments of the invention, but are not to be construed as limiting the invention in scope.

Example 4

SKF7™ is the only active ingredient used in the manufacture of the dietary supplement or pharmaceuticals. Other formulation ingredients may be added as necessary to produce the finished product. The final commercial product containing SKF7™ may use additional ingredients, such as maltodextrin. Any excipients or other additions will be approved food additives, Generally Recognized As Safe (GRAS) ingredients, or ingredients listed in "Capsule and

TABLE 1

| No | Ingredient | Capsule Quantity | Function | Ratio/Proportions |
|---|---|---|---|---|
| 1 | SKF7 ® *Labisia pumila* Extract (Standardised to Gallic Acid) | 187.5 mg (3.294 mg-4.456 mg Gallic Acid) | Active | 58.6% |
| 2 | Tricalcium Phosphate | 12.8 mg | Glidant | 4% |
| 3 | Silicon Dioxide | 3.2 mg | Glidant | 1% |
| 4 | Premix: Microcrystalline Cellulose (97-99%) and Glyceryl Monostearate (1-3%) | 48 mg | Diluent | 15% |
| 5 | Microcrystalline Cellulose | 68.5 mg | Binder | 21.4% |
|  | Total | 320 mg | Total | 100% |

SKF7™ had undergone steps to prove its safety by complying to international standards.

SKF7™ was tested and in compliance of the following studies:
List of Safety And Toxicity Studies (OECD and ICH-GCP Compliant)
  1. Bacterial Reverse Mutation Test
  2. In Vitro Mammalian Chromosome Aberration Test
  3. In Vitro Mammalian Micronucleus Test
  4. Mammalian Erythrocyte Micronucleus Test
  5. Repeated Dose 90-Day Oral Toxicity Study In Rodents
  6. Repeated Dose 1-Year Oral Chronic Toxicity Study In Rodents
  7. Pharmacokinetic and Safety Clinical Study in Healthy Subjects
  8. Randomised Placebo-Controlled Human Clinical Studies in Obese Subjects.

In another preferred embodiment of the present invention, standardised *Labisia pumila* aqueous ethanolic extract in orally effective amount characterised in that said extract for reducing the progression of health problems selected from obesity wherein the effective amount of extract orally taken ranges from 180 mg to 1500 mg per day for a period of 7 days to more than 12 months. Standardized *Labisia pumila* aqueous ethanolic extract for use wherein the effective amount of extract orally taken for acceptable daily intake is—for human in a range 180 mg to 1500 mg as per clinical Tablet Ingredients" of "NNFA List of Dietary Supplement Ingredients In Use Before Oct. 15, 1994." This facility complies with current Good Manufacturing Practices (cGMP) to produce traditional medicines. Labeesity, a commercial product containing SKF7™, is approved by the Ministry of Health for sale in Malaysia as a traditional medicine. This product is in the form of capsules containing either 90 or 187.5 mg SKF7.
Anti-Inflammatory Treatment SKF7™ and other *Labisia pumila* extracts have been shown to have anti-inflammatory activities and were shown to inhibit and suppress the above cytokines and biomarkers in multiple studies [Ahmad et al. (2020)]. SKF7™ is the only *Labisia pumila* extract that has undergone extensive safety and efficacy studies, and currently undergoing multi-sites and multi-countries Clinical Trials for Obesity under international ICH guidelines and is produced in a PIC/S GMP manufacturing facility.

TNF-$\alpha$ and IL-1 are also associated with obesity and T2DM [Alzamil (2020); Jung et al. (2014); Febbraio (2014)]. In in vivo studies, SKF7™ has been shown to have efficacy in anti-obesity models and other *Labisia pumila* extracts were also shown to have efficacy against T2DM. SKF7™ is also tested in an anti-diabetes study in vivo and is currently undergoing analysis. The relevant studies for SKF7™ and selected *Labisia pumila* extracts are explained in the following descriptions.

SKF7™ Data: Interleukin-1 for Anti-Inflammatory

Figure 8:
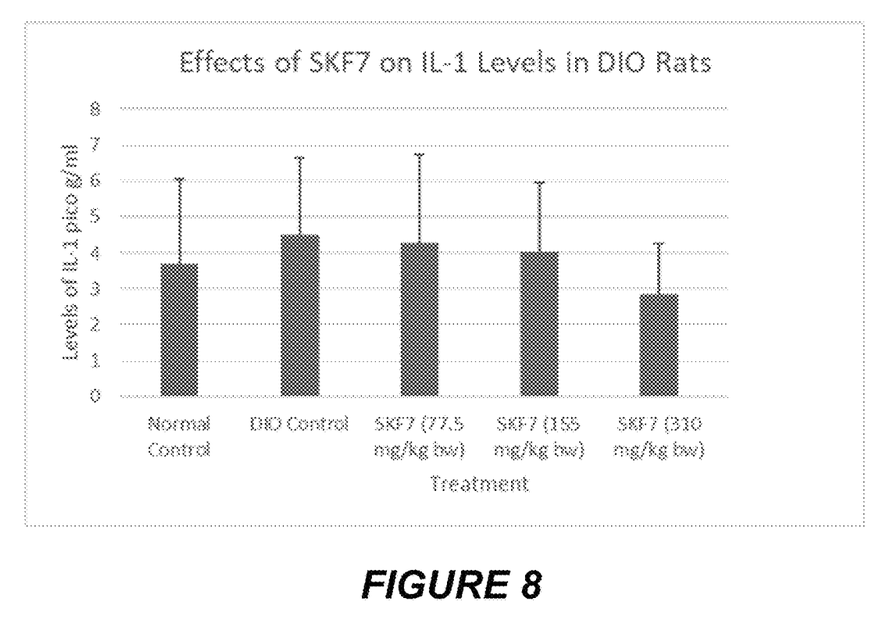
FIG. 8 illustrates In vivo study was conducted on SKF7™ treated rats, comparing to normal rat and Diet-Induced Obese (DIO) rats for anti-inflammatory treatment in accordance of the present invention.

In vivo study was conducted on SKF7™ treated rats, comparing to normal rat and Diet-Induced Obese (DIO) rats. SKF7™ 77.5 mg/kg, 155 mg/kg and 310 mg/kg revealed a reduction of interleukin-1 (IL-1) as compared to DIO control group by 4.5%, 10.3%, and 36.7% (P≤0.05), respectively as illustrated in FIG. 8.

Anti-Oxidant Treatment

Oxidative stress is highly correlated with a wide variety of inflammatory and metabolic disease states, including obesity. It is highly correlated with cumulative damage in the body done by free radicals inadequately neutralised by antioxidants. Furthermore, oxidative damage is aggravated by the decrease in antioxidant enzymes activities such as glutathione S-transferase (GST) and glutathione peroxidase (GPx) which acts as a free radical scavenger in conditions associated with oxidative stress.

Figure 9:
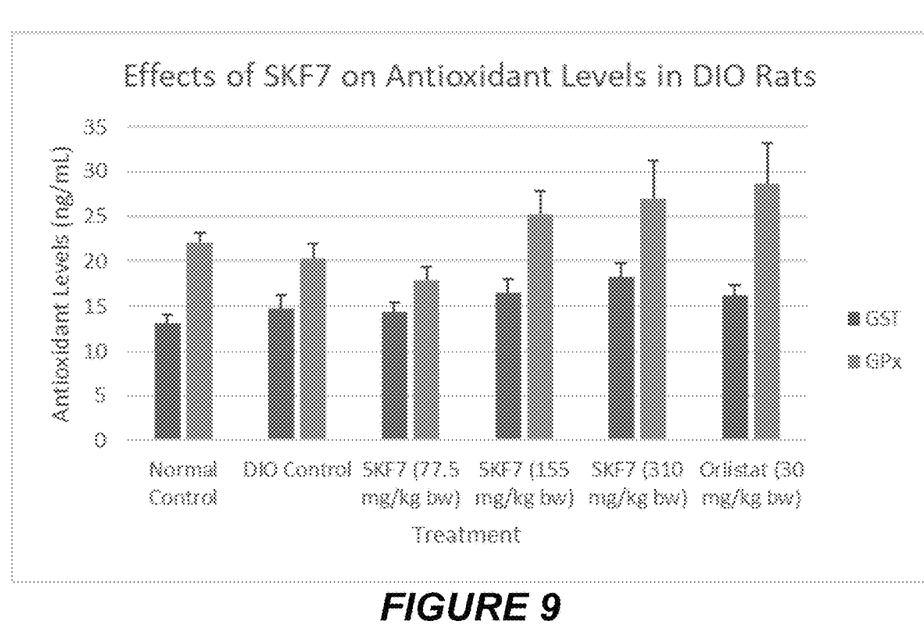
FIG. 9 illustrates In vivo study was conducted on SKF7™ treated rats, comparing to normal rat and Diet-Induced Obese (DIO) rats for anti-oxidant treatment in accordance of the present invention.

Treatment in SKF7™ 155 mg/kg, SKF7™ 310 mg/kg and Orlistat 30 mg/kg groups revealed a significant (P≤0.01) increase in GPx as compared to DIO control group by 24.5%, 33.2% and 40.9%, respectively. Meanwhile, SKF7™ 155 mg/kg, SKF7™ 310 mg/kg and Orlistat 30 mg/kg groups induced a significant increase in GST as compared to DIO control group by 12.9% (P≤0.05), 24.1% (P≤0.01) and 10.4% (P≤0.05), respectively as illustrated in FIG. 9. The induction of GPx and GST are contributed to control hydroxyl radicals and thus preventing lipid peroxidation and its propagation to biological membranes causing cells injury.

Inhibitory Ghrelin Production Levels

Figure 10:
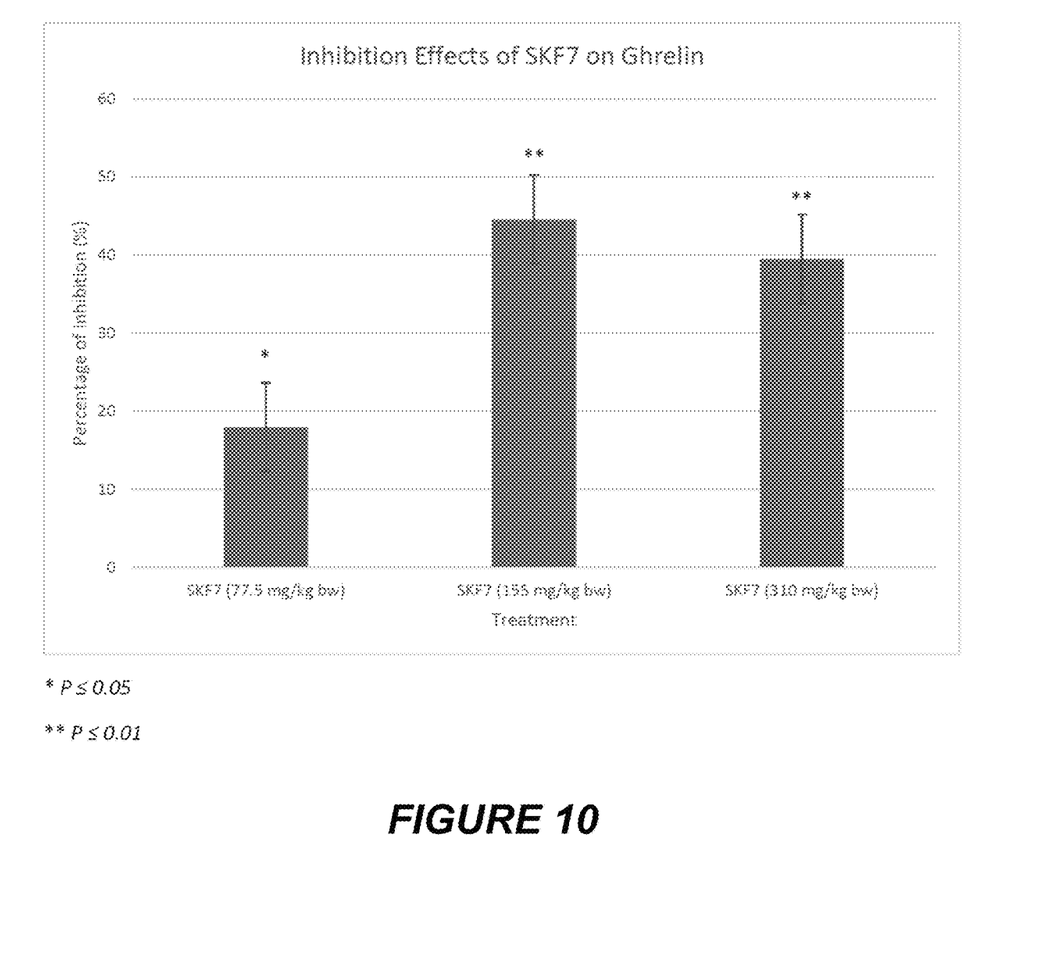
FIG. 10 illustrates In vivo study was conducted on SKF7™ treated rats, comparing to normal rat and Diet-Induced Obese (DIO) rats for suppression of Ghrelin production levels in accordance of the present invention.

Ghrelin levels were significantly reduced in animals treated with SKF7™ 77.5 mg/kg, SKF7™ 155 mg/kg, SKF7™ 310 mg/kg groups as compared to DIO control group by 18.0% (P≤0.05), 44.5% (P≤0.01), 39.5% (P≤0.01) and, respectively as shown in FIG. 10. Weight loss induce significant increases in the concentration of ghrelin, a potent orexigenic hormone. Elevations in ghrelin concentration, either endogenous or exogenous, are associated with feelings of hunger and increased food intake. Interestingly, SKF7™ inhibits ghrelin production levels while inducing weight loss. Hence, no significant changes were observed in average daily feed consumption in all groups.

The foregoing detailed description and examples are merely illustrative of the preferred embodiments. They are by no means meant to be the exclusive description of the inventive concept hereby disclosed. It will be recognized by one of ordinary skill in the art that certain aspects of the practice of the invention are readily susceptible to modification or practice by alternative, known means.

REFERENCES

1. Abdullah, N., Hosseinpour Chermahini, D. S., Chua, L. S. and Sarmidi, M. *Labisia pumila*: A review on its traditional, phytochemical and biological uses, 2013.
2. Hu, J., Webster, D., Cao, J. and Shao, A. (2018) The safety of green tea and green tea extract consumption in adults—Results of a systematic review. *Regulatory Toxicology and Pharmacology*. 95: 412-433.
3. Ahmad et al. (2020) Antioxidant and Anti-inflammatory Activities of Marantodes *pumilum* (Blume) Kuntze and Their Relationship with the phytochemical content.
4. Alzamil (2020) Elevated Serum TNF-α Is Related to Obesity in Type 2 Diabetes Mellitus and Is Associated with Glycemic Control and Insulin Resistance.
5. Jung et al. (2014) Obesity and Its Metabolic Complications: The Role of Adipokines and the Relationship between Obesity, Inflammation, Insulin Resistance, Dyslipidemia and Nonalcoholic Fatty Liver Disease.
6. Febbraio (2014) Role of interleukins in obesity: implications for metabolic disease.

The invention claimed is:

1. A process for making a *Labisia pumila* extract consisting essentially of:
   a) extracting dried *Labisia pumila* with aqueous ethanol at a ratio of between 1:5 to 1:20, respectively, in weight/volume at a temperature of 60° C.-100° C. for 2-6 hours in an extraction chamber to obtain a first extract;
   b) filtering the first extract to obtain a first filtrate and a first plant residue;
   c) re-extracting the first plant residue with aqueous ethanol at a temperature of 60° C.-100° C. for 2-6 hours in the extraction chamber to obtain a second extract;
   d) filtering the second extract to obtain a second filtrate and a second plant residue;
   e) concentrating the first extract and the second extract;
   f) mixing the first concentrated extract and the second concentrated extract to form the *Labisia pumila* extract;
   g) homogenizing the *Labisia pumila* extract with maldodextrins; and
   h) spray-drying the *Labisia pumila* extract, wherein the dried *Labisia pumila* extract is prepared by drying leaves of the *Labisia pumila* plant at 40° C.-55° C. for 5 hours until a moisture content is 6%-8%; drying stems and roots of the Labisia pumila plant at 40° C.-55° C. for 6 hours until a moisture content is 6%-8%; and grinding the dried leaves, stems and roots of the *Labisia pumila* plant to a particle size of 2 mm-4 mm.

2. The process of claim 1, wherein the aqueous ethanol is water and ethanol at a volumetic ratio of 1:1.

3. The process of claim 1, wherein the concentrating for the first extract is performed at a temperature of 80° C., pressure at 0.02 MPa for 50 minutes in a concentration chamber.

4. The process of claim 1, wherein the concentrating for the second extract is performed at a temperature of 80° C., pressure at 0.02 MPa for 80 minutes in a concentration chamber.

5. The process of claim 1, wherein the spray-drying is performed at an inlet temperature of 150-170° C. and an outlet temperature of 80-110° C. for 12 hours with a feed pump flow rate of 35-50 RPM.

* * * * *